United States Patent [19]

Mendelson et al.

[11] Patent Number: 5,075,341

[45] Date of Patent: Dec. 24, 1991

[54] TREATMENT FOR COCAINE ABUSE

[75] Inventors: Jack H. Mendelson; Nancy K. Mello, both of Rockport, Mass.

[73] Assignee: The McLean Hospital Corporation, Belmont, Mass.

[21] Appl. No.: 441,913

[22] Filed: Dec. 1, 1989

[51] Int. Cl.$^5$ .............................................. A61K 31/44
[52] U.S. Cl. ..................................... 514/282; 514/812
[58] Field of Search ................................ 514/812, 282

[56] References Cited

PUBLICATIONS

Chem. Abst.-110-166068t (1989).
Chem. Abst. 99-16461f (1983).
Lukas et al., *Clin. Pharmacol. Ther.* 36(1):127-132 (Jul. 1984).
Bickel et al., *Journal of Pharmacol. and Exper. Therapeutics* 247(1):47-53 (1988).
Kosten et al., *Life Sciences* 42:635-641 (1988).
O'Brien et al., *J. Clin Psychiatry* 49:2(Suppl):17-22 (Feb. 1988).
Gawin et al., *The New England Journal of Medicine* 318(18):1173-1182 (May 5, 1988).
Lukas et al., *Journal of Pharmacol. and Exper. Therapeutics* 238(3):924-931 (1986).
Kosten et al., *Am. J. Drug Alcohol Abuse* 12(1&2):1-16 (1986).
Kosten et al., *Life Sciences* 44:887-892 (1989).
Mello et al., "Buprenorphine Suppresses Cocaine Self-Administration in Rhesus Monkeys" (Abstract Only) (1989).
Kleber et al., *J. Clin. Psychiatry* 45:12(Sec. 2):18-23 (Dec. 1984).
Kosten et al., *Arch. Gen. Psychiatry* 44:281-284 (Mar. 1987).

*Primary Examiner*—Stanley J. Friedman
*Attorney, Agent, or Firm*—Sterne, Kessler, Goldstein & Fox

[57] ABSTRACT

Mixed opiate agonist/antagonists, particularly buprenorphine, is provided for the treatment of cocaine dependence and concurrent cocaine and opiate abuse and dependence.

10 Claims, No Drawings

TREATMENT FOR COCAINE ABUSE

This invention was made with government support under 2S07RR04484 awarded by NIH and 2K05DA00101, 5P50DA04059, 5K05DA00064, 5R01DA02519, and 5K02DA00115 awarded by ADAMHA. The government has certain rights in the invention.

BACKGROUND OF THE INVENTION

1. Field of the Invention

The invention is drawn to methods for the treatment of drug abuse, particularly cocaine and dual cocaine and opiate, abuse and dependence.

2. Brief Description of the Background Art

Cocaine abuse has reached epidemic proportions in the general population (Kozel, N. J., et al., *Science* 234:970 (1986); *National Institute on Drug Abuse. ADAMHA, Request for Application DA-89-01* (1988)) and has also increased among heroin-dependent persons, including those in methadone maintenance treatment programs (Kosten, T. R., et al., *Am. J. Drug Alcohol Abuse* 12:1 (1986); Kaul, B., et al., ibid. 8:27 (1981)). The many adverse medical consequences of cocaine abuse (Cregler, L. L., et al., *N. Engl. J. Med.* 315:1495 (1986); Mendelson, J. H., et al., *Harrison's Principles of Internal Medicine.* McGraw-Hill, New York (1986)) are further augmented by the combined use of cocaine and heroin (Kreek, M. J., *Psychopharmacology: The Third Generation of Progress.* Raven, New York (1987)). Dual addiction to intravenous cocaine and heroin use is likely to increase risk for AIDS, both through needle sharing and through the combined immuno-suppressive effects of both drugs (Donahoe, R. M., et al., *Psychological, Neuropsychiatric and Substance Abuse Aspects of AIDS.* Raven, New York (1988); Klein, T. W., et al. ibid (1988)). Intravenous drug abuse was estimated to account for over 30% of AIDS victims in the United States in 1988 (Kozel, N. J., et al., *Science* 234:970 (1986); *National Institute on Drug Abuse. ADAMHA, Request for Applications DA-89-01* (1988)).

At present, there is no uniformly effective pharmacotherapy for cocaine abuse (Kleber, H. D., et al. *J Clin. Psychiatry* 45:18 (1984); Gawin, F. H., et al., *N. Eng. J. Med.* 318:1173 (1988)), and the dual abuse of cocaine plus heroin is an even more difficult treatment challenge. Heroin abuse can be treated with opiate agonists (methadone and 1-alpha-acetylmethadol [LAAM]) (Dole, V. P., et al., *J. Am. Med. Assoc.* 193:646 (1965); Blaine, J. B., et al., *Recent Developments in Chemotherapy of Narcotic Addiction. Ann. New York. Acad. Sci.* 311:214 (1978); Blaine, J. B., et al., *Research Developments in Drug and Alcohol Use. Ann. New York. Acad. Sci.* 362:101 (1981)) and the opiate antagonist naltrexone (Meyer, R. E., et al., *The Heroin Stimulus,* Plenum, New York (1979); Martin, W. R., et al., *Arch. Gen. Psychiatry* 28:784 (1973); Mello, N. K., et al., *J. Pharmocol. Exp. Ther.* 216:45 (1981)), but these pharmacotherapies have not proved useful for combined cocaine and heroin abuse (Kosten, T. R., et al., *Arch. Gen. Psychiatry* 44:281 (1987)). Although desipramine (a tricyclic antidepressant) reduces cocaine abuse in some patients (Kleber, H. D., et al. *J. Clin. Psychiatry* 45:18 (1984); Gawin, F. H., et al., *N. Eng. J. Med.* 318:1173 (1988); Gawin, F. H., et al., *Arch. Gen. Psychiatry* 41:903 (1984); Tennant, F. S., et al., *Problems of Drug Dependence,* 1982. Committee on Problems of Drug Dependence, Washington, D.C. (1983)), it may stimulate relapse to cocaine abuse in abstinent patients (Weiss, R. E., *J. Am. Med. Assoc.* 260:2545 (1988)). Treatment with methadone and desipramine has yielded inconsistent results on cocaine use by heroin abusers (O'Brien, C. P., et al., *J. Clin. Psychiatry* 49:17 (1988); Kosten, T. R., et al., ibid 48:442 (1987)).

The present invention provides methods utilizing pharmacotherapies which antagonize the reinforcing effects of cocaine and has minimal adverse side effects or potential for abuse liability.

SUMMARY OF THE INVENTION

The present invention is drawn to compositions and methods for the treatment of drug abuse, particularly cocaine use and dependence, as well as concurrent cocaine and opiate use and dependence. Opioid mixed agonist-antagonists are provided, particularly buphenorphine, as effective pharmacotherapies for drug abuse treatments.

DETAILED DESCRIPTION OF THE SPECIFICATION EMBODIMENTS

In accordance with the present invention, compositions and methods are provided for the treatment of cocaine and/or cocaine and opiate abuse and dependence. The methods employ opioid mixed agonist-antagonists to suppress drug use by addicts.

The particular pharmacotherapies or narcotics useful in the present invention are opioid mixed agonist-antagonists. The subject pharmacotherapies antagonize the reinforcing effects of cocaine and are virtually devoid of toxic effects during chronic administration. Further, they do not lead to significant physical dependence and their administration can be terminated with minimal withdrawal symptoms.

Of particular interest as an effective pharmacotherapy is buphenorphine. Buphenorphine is a narcotic having morphine-like agonistic properties with respect to analgesia, physiological and subjective reactions, having opiate antagonistic action and producing minimal or no physical dependence. Buprenorphine is an oripavine derivative of thebaine with partial $\mu$ opioid agonist activity. It is a congener of a potent opioid agonist, etorphine, and an opioid antagonist, diprehorphine. The structure and chemical derivation of this opioid mixed agonist-antagonist have been described by J. W. Lewis in *Narcotic Antagonists: Advances in Biochemical Pharmacology.* M. Braude et al., eds. (Raven, New York. 1974), vol. 8, pp. 123-126 and Lewis et al. in *Advances in Substance Abuse. Behavioral and Biological Research.* N. K. Mello, ed. (JAI, Greenwich, Conn., 1983), vol. 3, pp. 103-154, which disclosures are herein incorporated by reference.

In general, buprenorphine is an ideal pharmacotherapy for the treatment of cocaine and/or cocaine and opiate abuse. Buprenorphine antagonizes the reinforcing effects of cocaine and has minimal adverse side effects or potential for abuse liability. Further, buprenorphine effectively suppresses heroin self-administration by heroin dependent abusers as demonstrated by in-patient studies. Importantly, the cessation of buprenorphine treatment does not produce severe and protracted withdrawal signs and symptoms in man. Buprenorphine is safer than methadone, since its antagonist component appears to prevent lethal overdose, even at approximately ten times the analgesic therapeutic dose. Buprenorphine is also effective for the outpatient detoxification of heroin-dependent persons.

Thus, buprenorphine is also valuable for the treatment of dual addiction to cocaine and heroin. Buprenorphine's opioid agonist effects make it acceptable to heroin abusers, but illicit diversion is minimal in comparison to heroin.

As indicated, while the pharmacotherapies find particular use in the treatment of cocaine abuse, they are also effective in the treatment of cocaine and opiate abuse. Accordingly, the compositions find use as agents for drug detoxification, for the suppression of cocaine and cocaine and opiate self-administration, in the tapering from other drug substitute programs, such as methadone, and other related uses. The present invention may therefore be used in combination with other drug abuse programs.

The pharmacotherapies implicated as useful for the treatment of cocaine and dual cocaine and opiate abuse can be further tested in clinical evaluations to confirm their effectiveness. One means available for evaluation is a double-blind (pharmacotherapy versus placebo) trial with randomized patient assignment and independent indices of compliance with the treatment regimen and objective measures of drug use. Indices of compliance with the regimen can be determined, for example, by measuring levels of the pharmacotherapy in the blood. Objective measures of drug use can be measured by drug urine screens.

Methods of treatment involve the administration of selected pharmacotherapies in a sufficient dosage to decrease or eliminate the self-administration of cocaine and/or opiates. At the same time, the dosage should not be so high to produce any undesirable side effects, such as nausea, vomiting, dizziness, headaches, etc.

The particular dosage will vary according to the particular pharmacotherapy being administered, the frequency and method of administration, concurrent medication, physical condition and body weight of the subject receiving the dosage, and the like. For the most part, the dosage will range from about 0.02 to about 1.50 mg/kg of the subject body weight/day, usually about 0.05 to about 0.90 mg/kg/day. The dosage may be provided in a single dose or alternatively in divided doses.

The pharmacotherapy is provided, usually on a daily basis for a period of time to effectively suppress drug abuse, usually for about 15 to about 60 days. At this time, the administration of the pharmacotherapy may be tapered by decreasing the concentration administered on a daily basis. In this manner, the subject is gradually detoxified to a drug-free state. While the administration of some pharmacotherapies, such as buprenorphine, may be terminated with minimal withdrawal symptoms, a gradual detoxification is generally preferred.

The method of administration of the pharmacotherapies may vary. For the most part, however, the drugs will be administered sublingually or subcutaneously. Therefore, the pharmacotherapies are provided in dosage forms such as tablets, capsules, powders, liquid solutions, or formulations, etc.

In general, the pharmacotherapies of the present invention are available commercially. For example, buprenorphine may be purchased as Buprenex® from suppliers including Norwich Eaton Pharmaceuticals, Inc.

While the pharmacotherapy may be administered as a single agent, it may also be combined with other suitable components to provide a formulation for administration. In this regard, the particular narcotic may be dissolved in an alcohol or other appropriate solution. Additionally, other pharmacologically acceptable components such as carriers, stabilizers, sugars, buffers, pH adjusters may be included in the formulation.

To aid in the detoxification of the subject, where the pharmacotherapy is administered sublingually, a flavoring component may be added to the formulation to mask the presence of the particular pharmacotherapy. In this manner, the concentration of the pharmacotherapy can then be decreased without detection by the subject. Suitable flavoring components are known and are available in the art.

As noted, buprenorphine is recognized as a particularly effective pharmacotherapy. For use in the subject method, buprenorphine will typically be administered by the sublingual or subcutaneous route. Generally, buprenorphine doses are more potent when delivered sublingually.

For sublingual administration, buprenorphine is prepared in an appropriate aqueous solution, usually an aqueous ethanol or alcohol solution as provided by Bicket et al., *J. Pharm. Exp. Ther.* 247:47-53 (1988), and Kosten et al., *Life Sci.* 42:635-641 (1988). Additional components, as discussed above, may be included. A sample preparation involves, for example, 4 mg of buprenorphine base dissolved in one ml of a mixture of 95% alcohol (30%) and a citrate phosphate buffer (70%, pH 5). This solution may be prepared and stored for about 2 to about 3 weeks in opaque sealed containers.

The prepared solution is administered sublingually in a constant volume of about 1 ml. During administration, the subject is required to hold the solution under his/her tongue for a period of time from about 5 min to about 20 min, usually about 8 min to about 12 min.

For subcutaneous administration, the buprenorphine is dissolved as described in an appropriate aqueous solution and the pH adjusted to about pH 4 to about pH 6, usually about pH 4.5. The solution is then ready for injection into the subject.

During the duration of treatment described herein, the subjects receiving the treatment can be monitored to determine the overall effect of the pharmacotherapy. In this manner, dosages can be increased or decreased to provide the most effective dosage for a particular subject. Monitoring will include respiratory and pulse rates, blood pressure, and temperature. Further, subjects can be monitored for abstinence (scored according to Himmelsbach, C. K., *J. Pharmacol. Exp. Ther.* 67:239-249 (1939)), loss of weight, etc. The success in abstinence from illicit drugs can be monitored by urine testing of the subjects.

The above disclosure generally describes the present invention. A more complete understanding can be obtained by reference to the following specific examples which are provided herein for purposes of illustration only and are not intended to be limiting unless otherwise specified.

EXPERIMENTAL

The effects of buprenorphine treatment on cocaine self-administration by rhesus monkeys has been examined Cocaine effectively maintains operant responding leading to its intravenous administration in the primate model. As it is well established that primates self-administer most drugs abused by man (Thompson, T., et al., *Predicting Dependence Liability of Stimulant and Depressant Drugs.* University Park Press, Baltimore, Md. (1977); Griffiths, R. R., et al., *Advances in Substance*

Abuse. Behavioral and Biological Research Vol. 1, JAI Press, Greenwich, Conn. (1980); Griffiths, R. R., et al., Clin. Pharmacol. Ther. 25:61 (1979)), the primate model of drug self-administration is a useful method for the prediction of drug abuse liability and can be used to evaluate new pharmacotherapies for drug abuse disorders (Mello, N. K., et al., J Pharmacol. Exp. Ther. 225:378 (1983)).

Two male and three female adult rhesus monkeys (*Macaca mulatta*) with a 262±79 day history of cocaine self-administration were studied. Animal maintenance and research was conducted in accordance with guidelines provided by the Committee on Laboratory Animal Resources. The facility is licensed by the U.S. Department of Agriculture and protocols were approved by the Institutional Animal Care and Use Committee. The health of the animals was periodically monitored by a consultant veterinarian from the New England Regional Primate Research Center. Surgical implantation of an intravenous catheter for drug infusion was performed under aseptic conditions. A surgical level of anesthesia was induced with ketamine (25 mg/kg, i.m.) or pentobarbital (30 mg/kg, i.v.). Since the procedure usually takes 25 min, supplemental doses of anesthetic were seldom required. A mild analgesic (Tylenol) was administered every 4 to 6 hours for the first 24 hours after surgery. Each monkey was surgically implanted with a double lumen silicone rubber intravenous catheter under aseptic conditions to permit administration of buprenorphine or saline during cocaine self-administration. The intravenous catheter was protected by a custom-designed tether system (Spaulding Medical Products) that permits monkeys to move freely. Monkeys worked for food (1-g banana pellets) and for intravenous cocaine (0.05 or 0.10 mg per kilogram of body weight per injection) on the same operant schedule of reinforcement. An average of 64 responses was required for each food pellet or cocaine injection under a second order schedule of reinforcement (Completion of a fixed ratio (FR) of four consecutive variable ratio (VR) components, in which an average of 16 responses produced a brief stimulus light (S+), was required for cocaine or food delivery. This is a second-order FR 4 schedule with VR 16 components (FR 4 [VR 16:S]). Food and cocaine each were available during four 1-hour sessions at 12 noon, 4 p.m., 8 p.m., and 8 a.m. Each food or drug session lasted for 1 hour or until 20 drug injections or 65 food pellets were delivered. The total number of cocaine injections was limited to 80 per day to minimize the possibility of adverse drug effects. The nutritionally fortified banana pellet diet was supplemented with fresh fruit, vegetables, biscuits, and multiple vitamins each day.

Buprenorphine treatment was administered at two doses (0.40 and 0.70 mg/kg/day) that effectively suppressed opiate self-administration in our previous studies in the primate model (Mello, N. K., et al., J. Pharmacol. Exp. Ther. 225:378 (1983)). Each dose of buprenorphine and saline was studied for 15 consecutive days (60 sessions). After 30 days of treatment, buprenorphine was abruptly discontinued and daily saline treatment was resumed. Buprenorphine (or an equal volume of saline control solution) was administered daily beginning at 9:30 a.m. Buprenorphine and saline were gradually infused at a rate of 1 ml of solution every 12 min and flushed through the catheter with sterile saline in a volume that exceeded the estimated catheter dead space.

Cocaine and food self-administration were measured during 15 days of saline treatment and six successive 5-day periods of buprenorphine treatment. Each of the five monkeys self-administered relatively high doses of cocaine during base-line saline-treatment (2.1 to 4 mg/kg/day; group average [±S.E.M.] of 3.07±0.17 mg/kg/day). This level of cocaine self-administration corresponds to that commonly reported by cocaine abusers (1 to 2 gm/week is equivalent to 2.04 to 4.08 mg/kg/day in man) (Mendelson, J. H., et al., Am. J. Psychiatry 145:1094 (1988)). All animals reduced their cocaine self-administration significantly during buprenorphine treatment ($P < 0.0001$). On the first day of buprenorphine treatment, cocaine self-administration decreased by 50% or more in 4 of the 5 subjects (range 50 to 67%). Average cocaine self-administration decreased by 49 (±15.5)% to 1.60±0.25 mg/kg/day during the first 5 days of buprenorphine treatment ($P < 0.01$). Average cocaine self-administration then decreased to 77 (±7.4)% and 83% (±8.2)% below base-line levels during buprenorphine treatment days 6 to 10 and 11 to 15, respectively. Cocaine self-administration averaged 0.98±0.11 mg/kg/day over the first 15 days of buprenorphine treatment at 0.40 mg/kg/day.

During the second 15 days of buprenorphine treatment at 0.70 mg/kg/day, cocaine self-administration decreased to between 91 (±2.7)% and 97 (±0.9)% below base-line levels. Monkeys self-administered an average of 0.19±0.03 mg/kg/day of cocaine. Analysis of individual subject data showed that the rate and degree of buprenorphine's suppression of cocaine-maintained responding was equivalent in animals that self-administered relatively high (4 mg/kg/day) and low (2.1 mg/kg/day) doses of cocaine during the saline base-line treatment period. Cocaine-maintained operant responding remained suppressed for at least 15 days after cessation of buprenorphine treatment. This time course is similar to clinical reports of abstinence signs and symptoms 15 to 21 days after abrupt withdrawal of buprenorphine (Jasinski, D. R., et al., Arch. Gen. Psychiatry 35:601 (1978)) and probably reflects the slow dissociation of buprenorphine from the opiate receptor (Lewis, J. W., Narcotic Antagonists: Advances in Substance Abuse. Behavioral and Biological Research. Raven, New York, Vol. 8 (1974); Lewis, J. W., et al., Advances in Substance Abuse, Behavioral and Biological Research. JAI Press, Greenwich, Conn., Vol. 3 (1983)). Individual monkeys returned to base-line levels of cocaine self-administration at different rates ranging from 15 to 58 days (mean, 30.5±10 days).

In contrast to its dose-dependent effects on cocaine self-administration, buprenorphine administration (0.40 mg/kg/day) suppressed food-maintained responding by only 31 (±8.3)% during the first 15 days of treatment. Then food self-administration gradually recovered to average 20 (±12.5)% below base-line during the second 15 days of treatment with a higher dose of buprenorphine. Although these changes were statistically significant ($P < 0.05$ to 0.01) it is unlikely that they were biologically significant. There were no correlated changes in body weight and animals continued to eat daily fruit and vegetable supplements. Moreover, food self-administration during the first daily session after buprenorphine treatment was not suppressed in comparison to saline treatment. The distribution of food intake across the 4 daily food sessions was equivalent during saline and buprenorphine treatment conditions. Four of five animals returned to base-line levels of food-maintained operant responding within 3 to 17 days after cessation of buprenorphine treatment ($x = 8.5 \pm 2.9$ days). Animals were not sedated during buprenorphine treatment and activity levels appeared normal. These data suggest that buprenorphine treatment suppressed cocaine-maintained responding but did not produce a generalized suppression of behavior.

An advantage of the primate model for preclinical evaluation of pharmacotherapies is that compliance and multiple drug use are not at issue. It is important to emphasize that buprenorphine treatment of cocaine abuse would not be a "substitute addiction" with a less toxic cocaine-like stimulant drug analogous to methadone treatment of heroin dependence.

There is good consensus that dopaminergic neural systems play a critical role in cocaine reinforcement, and the data suggest that buprenorphine modifies the reinforcing properties of cocaine. This interpretation is consistent with several lines of evidence indicating co-modulatory interactions between endogenous opioid and dopaminergic systems in brain and behavioral studies suggest that dopaminergic systems modulate endogenous opioid system activity and the converse. Attenuation of cocaine self-administration by buprenorphine, an opioid mixed agonist-antagonist, further illustrates an inter-relationship between opioid and dopamine systems. The findings also suggest the importance of examining commonalities in the way in which abused drugs maintain behavior leading to their self-administration.

The current disclosure provides a major advance in drug treatment programs. Importantly, the use of buprenorphine or other opioid mixed agonist-antagonists is not simply a substitution of one addiction for another but rather is a true treatment of the cocaine or concurrent cocaine and opiate dependence. Accordingly, the benefits to society in terms of reduction of drug problems and the associated risks for HIV infection are incalculable.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for treating cocaine abuse and dependence in drug addicts comprising:
   administering to said addict an effective amount of buprenorphine to suppress drug abuse.

2. A method according to claim 1, wherein said effective amount comprises about 0.02 to about 1.50 mg/kg body weight/day.

3. A method according to claim 2, wherein said effective amount comprises about 0.05 to about 0.90 mg/kg body weight/day.

4. A method according to claim 1, wherein said administering comprises sublingual and subcutaneous administration.

5. A method according to claim 4, wherein said administering comprises subcutaneous administration.

6. A method for using buprenorphine for the treatment of drug abuse and dependence comprising: administering to humans abusing or addicted to cocaine an effective amount of buprenorphine to suppress drug abuse.

7. A method according to claim 6, wherein said effective amount comprises about 0.02 to about 1.50 mg/kg body weight/day.

8. A method according to claim 6, wherein said effective amount comprises about 0.05 to about 0.90 mg/kg body weight/day.

9. A method according to claim 6, wherein said administering comprises sublingual and subcutaneous administration.

10. A method according to claim 9, wherein said administering comprises subcutaneous administration.

* * * * *